(12) United States Patent
Chen et al.

(10) Patent No.: US 10,604,528 B2
(45) Date of Patent: Mar. 31, 2020

(54) GALUNISERTIB CRYSTALLINE FORM, PREPARATION METHOD THEREOF AND USE THEREOF

(71) Applicant: Crystal Pharmaceutical (Suzhou) Co., Ltd., Suzhou, Jiangsu (CN)

(72) Inventors: Minhua Chen, Suzhou (CN); Yanfeng Zhang, Suzhou (CN); Yuhao Chen, Suzhou (CN); Hui Gao, Suzhou (CN); Fei Lu, Suzhou (CN); Xiaoyu Zhang, Suzhou (CN)

(73) Assignee: Crystal Pharmaceutical (Suzhou) Co., Ltd., Suzhou (CN)

( * ) Notice: Subject to any disclaimer, the term of this patent is extended or adjusted under 35 U.S.C. 154(b) by 0 days.

(21) Appl. No.: 16/315,242

(22) PCT Filed: Jul. 21, 2017

(86) PCT No.: PCT/CN2017/092233
§ 371 (c)(1),
(2) Date: Jan. 4, 2019

(87) PCT Pub. No.: WO2018/006870
PCT Pub. Date: Jan. 11, 2018

(65) Prior Publication Data
US 2019/0241572 A1    Aug. 8, 2019

(30) Foreign Application Priority Data
Jul. 7, 2016 (CN) .......................... 201610533326

(51) Int. Cl.
| C07D 487/04 | (2006.01) |
| A61P 35/00 | (2006.01) |
| A61K 31/4162 | (2006.01) |
| A61K 31/4709 | (2006.01) |

(52) U.S. Cl.
CPC ........ *C07D 487/04* (2013.01); *A61K 31/4162* (2013.01); *A61K 31/4709* (2013.01); *A61P 35/00* (2018.01); *C07B 2200/13* (2013.01)

(58) Field of Classification Search
CPC ........................... C07D 401/14; C07D 487/04
USPC ........................................... 546/167; 514/314
See application file for complete search history.

(56) References Cited

U.S. PATENT DOCUMENTS 6,627,646 B2 * 9/2003 Bakale ................. C07D 401/12
514/303

FOREIGN PATENT DOCUMENTS

CN          1714090 A       12/2005
WO     2007/018818 A1       2/2007

OTHER PUBLICATIONS

CMU Pharmaceutical polymorphism, internet p. 1-3 (2002) printout Apr. 3, 2008.*
Singhal et al., "Drug Polymorphism, etc.," Advanced Drug Delivery reviews 56, p. 335-347 (2004).*
Concise Encyclopedia Chemistry, NY: Walter de Gruyter, 1993, 872-873.*
Jain et al., "Polymorphism in Pharmacy", Indian Drugs, 1986, 23(6) 315-329.*
Muzaffar et al., "Polymorphism and Drug Availability, etc.," J of Pharm. (Lahore), 1979, 1(1), 59-66.*
U.S. Pharmacopia #23, National Formulary #18, 1995, 1843-1844.*
Doelker, english translation of S.T.P, Pratiques (1999), 9(5), 399-409, pp. 1-33.*
Doelker, english translation of Ann. Pharm. Fr., 2002, 60: 161-176, pp. 1-39.*
Taday et al., "Using Terahertz, etc.," J of Pharm. Sci., 92(4), 2003, 831-838.*
Osuka et al., "Effect of Polymorphic, etc.," Chem. Pharm. Bull., 47(6) 852-856 (1999).*
Niemeier et al., Application of Kinetic Modeling and Competitive Solvent Hydrolysis in the Development of a Highly Selective Hydrolysis of a Nitrile to an Amide. Org Process Res Dev. 2014;18(3):410-416.
International Search Report and Written Opinion for Application No. PCT/CN2017/092233, dated Sep. 28, 2017, 10 pages.

* cited by examiner

*Primary Examiner* — Patricia L Morris
(74) *Attorney, Agent, or Firm* — McCarter & English, LLP; Steven G. Davis; Wei Song (57) ABSTRACT

The present disclosure relates to a novel crystalline form of Galunisertib, processes for preparation and use thereof. The present disclosure also relates to a pharmaceutical composition comprises the novel crystalline form of Galunisertib and use of the novel crystalline form of Galunisertib and pharmaceutical composition for preparing drugs treating disease. The crystalline form of the present disclosure has good stability, solubility and hygroscopicity, which has significant value for future drug optimization and development.

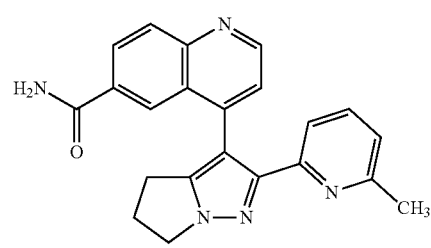

4 Claims, 5 Drawing Sheets

GALUNISERTIB CRYSTALLINE FORM, PREPARATION METHOD THEREOF AND USE THEREOF

CROSS-REFERENCE TO RELATED APPLICATIONS

The present application is a U.S. national stage application, filed under 35 U.S.C. § 371(c), of International Application No. PCT/CN2017/092233, filed on Jul. 21, 2017, which claims the priority of Chinese Application No. 201610533326.X, filed on Jul. 7, 2016. The entire contents of the aforementioned applications are incorporated herein by reference.

TECHNICAL FIELD

The present disclosure relates to the technical field of pharmaceutical crystal technology, particularly relates to the novel crystalline form of Galunisertib, processes for preparation and use thereof.

BACKGROUND

Transforming growth factor-β (TGF-β) is a pleiotropic cytokine with multiple tumor supporting effects, including angiogenesis and immunosuppression. The increase of TGF-β expression is closely related to the progression of various tumors and poor clinical prognosis. Expression of TGF-β promotes tumor growth, inhibits the immune system, and enhances tumor spread.

Galunisertib (LY-2157299) is a TGF-β kinase inhibitor developed by Eli Lilly, which has the potential to treat myelodysplastic syndromes and solid tumors. The chemical name of Galunisertib is 2-(6-methyl-pyridin-2-yl)-3-[6-amido-quinolin-4-yl)-5,6-dihydro-4H-pyrrolo[1,2-b]pyrazole, and the structure is shown in formula I.

Formula I

Polymorph or polymorphism is a particular property of certain molecule and molecular composition. Different crystalline forms of certain compounds arise from different molecular packing in the crystal lattice, and these crystalline forms have different crystal structures and physical properties, such as solubility; stability, thermal property, mechanical property, purification capability, X-ray diffraction pattern, infrared absorption spectroscopy, Raman spectroscopy, solid state nuclear magnetic resonance, etc. One or more analytical techniques can be used to distinguish different crystalline forms of the same molecule or molecular composition.

Novel crystalline forms (including anhydrates, hydrates and solvates) of the active pharmaceutical ingredients may offer better processing and physicochemical properties, such as bioavailability, stability, processability, and purification ability. Some novel crystalline forms may serve as intermediate crystal forms to facilitate solid state transformation to desired forms. Novel polymorphs of raw materials provide more solid forms in the formulation, and this can improve dissolution, improve shelf life, and make it easier to process.

A monohydrate crystalline form of Galunisertib (designated as Form 1 in the present disclosure) was disclosed in the patent application WO2007018818A1, which is hereby incorporated by reference. The X-ray powder diffraction pattern of Form 1 shows one or more characteristic peaks at 2theta values of 9.05°, 11.02°±0.1°, 11.95°±0.1°, and 14.84°±0.1°. However, the inventors of the present disclosure found an anhydrous crystalline form of Galunisertib (hereinafter referred to as Form A) during the research. The X-ray powder diffraction pattern of Form A shows characteristic peaks at 2theta values of 22.0°±0.2°, 10.4°±0.2°, and 25.3°±0.2°. Compared with the monohydrate Form 1 of the prior art, it has been found that Form A of the present disclosure has better solubility, hygroscopicity and stability. When Form 1 and Form A are placed in 80% RH, Form 1 is slightly hygroscopic. While Form A is non-hygroscopic or almost non-hygroscopic. In particular, Form A has a significant improvement in solubility compared to Form 1 of the prior art. For example, in FaSSIF (Fasted state simulated intestinal fluids, pH=6.5), the solubility of Form A is ten times higher than that of Form 1 at 24 h. The increase in solubility is beneficial to reduce drug load and improve the bioavailability of the drug products. No form change was observed for Form A of the present disclosure after being placed at 40° C./75% RH for one year or mechanical grinding, which indicates that Form A has good stability. Good stability can effectively avoid crystal transformation during drug storage and development, thus avoiding changes in bioavailability and efficacy.

SUMMARY

In order to overcome the disadvantages of prior arts, the main objective of the present disclosure is to provide a novel crystalline form of Galunisertib, processes for preparation and use thereof.

According to the objective of the present disclosure, a novel crystalline form of Galunisertib is provided (hereinafter referred to as Form A). The crystalline form of the present disclosure has high solubility, is almost non-hygroscopic and has good stability, which is suitable for industrial purification and production. Form A provided by the present disclosure is an anhydrite.

According to one aspect of the present disclosure, the X-ray powder diffraction pattern of Form A shows characteristic peaks at 2theta values of 22.0°±0.2°, 10.4°±0.2° and 25.3°±0.2° using CuKα radiation.

Furthermore, the X-ray powder diffraction pattern of Form A shows 1 or 2 or 3 characteristic peaks at 2theta values of 15.9°±0.2°, 14.7°±0.2° and 16.9°±0.2°. Preferably, the X-ray powder diffraction pattern of Form A shows characteristic peaks at 2theta values of 15.9°±0.2°, 14.7°±0.2° and 16.9°±0.2°.

Furthermore, the X-ray powder diffraction pattern of Form A shows 1 or 2 or 3 characteristic peaks at 2theta values of 19.5°±0.2°, 12.5°±0.2° and 20.0°±0.2°. Preferably, the X-ray powder diffraction pattern of Form A shows characteristic peaks at 2theta values of 19.5°±0.2°, 12.5°±0.2° and 20.0°±0.2°.

In a preferred embodiment, the X-ray powder diffraction pattern of Form A shows characteristic peaks at 2theta values of 22.0°±0.2°, 10.4°±0.2°, 25.3°±0.2°, 15.9°±0.2°, 14.7°±0.2°, 16.9°±0.2°, 19.5°±0.2°, 12.5°±0.2° and 20.0°±0.2°.

Figure 1:
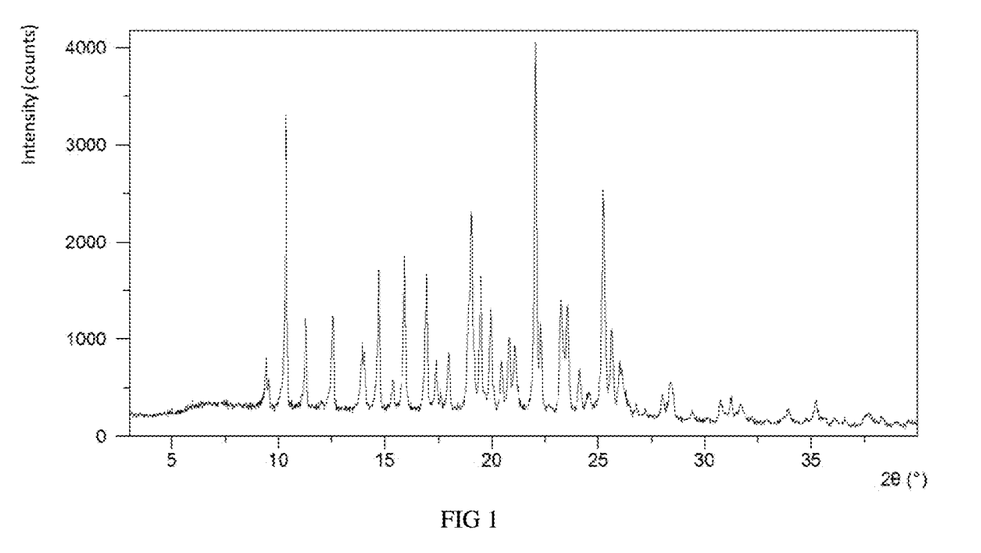
FIG. 1 shows an XRPD pattern of Form A in example 1.

Without any limitation being implied, in a specific example of the present disclosure, the X-ray powder diffraction pattern of Form A is substantially as depicted in FIG. 1.

According to the objective of the present disclosure, a process for preparing Form A is also provided. The process comprises: heating the solid of Galunisertib to 170° C.-240° C., and the obtained solid is Form A.

Preferably, said heating is heating to 180° C.

In the present disclosure, "crystal" or "crystalline form" refers to the crystal or the crystal form being identified by the X-ray diffraction pattern shown herein. Those skilled in the art are able to understand that physicochemical properties discussed herein can be characterized, wherein the experimental errors depend on the conditions of instruments, the sampling processes and the purity of samples. In particular, those skilled in the art generally know that the X-ray diffraction pattern typically vary with the experimental conditions. It is necessary to point out that, the relative intensity of the diffraction peaks in the X-ray diffraction pattern may also vary with the experimental conditions; therefore, the order of the diffraction peak intensities cannot be the sole or decisive factor. In fact, the relative intensity of the diffraction peaks in the X-ray powder diffraction pattern is related to the preferred orientation of the crystals, and the diffraction peak intensities shown herein are illustrative and not for absolute comparison. In addition, the experimental error of the diffraction peak position is usually 5% or less, and the error of the position should also be taken into account, and an error of ±0.2° is usually allowed. In addition, due to experimental factors such as sample thickness, the overall offset of the diffraction peak happened, and a certain offset is usually allowed. Thus, it will be understood by those skilled in the art that it is unnecessary that the X-ray diffraction pattern of a crystalline form of the present disclosure should be exactly the same as X-ray diffraction patterns of the example shown herein. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, crystalline Form A of the present disclosure is pure, singular and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

According to the objective of the present disclosure, a pharmaceutical composition is provided;

said pharmaceutical composition comprises a therapeutically and/or preventively effective amount of Form A and pharmaceutically acceptable carriers, diluents or excipients.

Furthermore, Form A of the present disclosure can be used for preparing drugs treating myelodysplastic syndromes.

Furthermore, Form A of the present disclosure can be used for preparing drugs treating solid tumors.

Furthermore, said pharmaceutical composition may also contain other pharmaceutically acceptable crystalline forms or amorphous of Galunisertib or salts thereof, including but not limited to, for example Form 1 disclosed in WO2007018818A1.

The Galunisertib Form A of the present disclosure has the following advantages:

Good solubility. The solubility of Form A in three buffers with different pH values is higher than that of Form 1 of the prior art;

Good stability. No form change was observed for Form A after being placed at 40° C./75% RH for one year or mechanical grinding. Form A has better stability than Form 1 at high temperature.

Non-hygroscopic or almost non-hygroscopic. Compared with Form 1 of the prior art, Form A has lower hygroscopicity. Form A is not susceptible to high humidity to deliquescence, which is beneficial for long-term storage of the drug.

Crystalline form with low hygroscopicity does not require special drying conditions in the preparation process, which simplifies the preparation and downstream process, and is easy for industrial production. Moreover, the water content of Form A remains substantially unchanged under different humidity conditions, which is beneficial to the long-term storage of the drug. Due to the non-strict requirements on storage conditions, the cost of drug storage and quality control will be greatly reduced, which has great economic value. Higher solubility helps to improve the absorption and availability of drugs in the body, improve drug efficacy and bioavailability.

DETAILED DESCRIPTION OF THE PRESENT DISCLOSURE

The present disclosure is further illustrated by the following examples which describe the preparation and use of the crystalline forms of the present disclosure in detail. It is obvious to those skilled in the art that many changes in the materials and methods can be accomplished without departing from the scope of the present disclosure.

Instruments and methods used to collect data:

The abbreviations used in the present disclosure are explained as follows:
XRPD: X-ray Powder Diffraction
DSC: Differential Scanning Calorimetry
TGA: Thermal Gravimetric Analysis
DVS: Dynamic Vapor Sorption
$^1$H NMR: Proton Nuclear Magnetic Resonance
PSD: Particle Size Distribution
HPLC: High Performance Liquid Chromatography X-ray powder diffraction pattern the present disclosure was acquired by a Panalytical Empyrean X-ray powder diffractometer. The parameters of the X-ray powder diffraction method of the present disclosure were as follows:
X-ray Reflection: Cu, Kα
Kα1 (Å): 1.540598; Kα2 (Å): 1.544426
Kα2/Kα1 intensity ration: 0.50
Voltage: 45 (kV)
Current: 40 (mA)
Scan range: from 3.0 degree to 40.0 degree Differential scanning calorimetry (DSC) data in the present disclosure were acquired by a TA Q2000. The parameters of the differential scanning calorimetry (DSC) method of the present disclosure were as follows:
Heating rate: 10° C./min
Purge gas: nitrogen Thermal gravimetric analysis (TGA) data in the present disclosure are acquired by a TA Q5000. The parameters of the thermal gravimetric analysis (TGA) method of the present disclosure were as follow:
Heating rate: 10° C./min
Purge gas: nitrogen Proton nuclear magnetic resonance spectrum data ($^1$H NMR) was collected from a Bruker Avance II DMX 400M HZ NMR spectrometer. 1-5 mg of sample was weighed, and dissolved in 0.5 mL of deuterated dimethyl sulfoxide to obtain a solution with a concentration of 2-10 mg/ML.

Unless otherwise specified, the following examples were conducted at room temperature The particle size distribution test in the present disclosure is acquired by the S3500 laser particle size analyzer of Microtrac. Microtrac S3500 is equipped with the SDC (Sample Delivery Controller). The test is carried out by wet process, and the dispersion medium is Isopar G. The parameters are as follow:

| | |
|---|---|
| Size distribution: Volume | Run Time: 10 s |
| Dispersion medium: Isopar G | Particle coordinates: Standard |
| Run Number: Average of 3 runs | Fluid refractive index: 1.42 |
| Particle Transparency: Trans | Residuals: Enabled |
| Particle refractive index: 1.59 | Flow rate: 60* |
| Particle shape: Irregular | Filtration: Enabled |

*Flow rate 60% is 60% of 65 mL/s.

Raw materials of Galunisertib used in the following examples are prepared by known methods in the prior art, for example, the method disclosed in WO2007018818A.

Example 1: Preparation of Form A 207.7 mg of Galunisertib solid was weighed into a 20-mL glass vial. The glass vial was placed into an oven at 180° C. for two hours and the solid was collected.

The obtained solid in this example was confirmed to be Form A. The X-ray powder diffraction data of the obtained solid are shown in Table 1, while the XRPD pattern is substantially as depicted in FIG. 1.

TABLE 1

| 2θ | d spacing | Relative intensity % |
|---|---|---|
| 9.42 | 9.39 | 12.85 |
| 10.35 | 8.55 | 80.20 |
| 11.27 | 7.85 | 24.24 |
| 12.54 | 7.06 | 24.48 |
| 14.69 | 6.03 | 39.47 |
| 15.36 | 5.77 | 8.26 |
| 15.92 | 5.57 | 43.90 |
| 16.94 | 5.23 | 36.21 |
| 17.39 | 5.10 | 13.66 |
| 17.99 | 4.93 | 14.59 |
| 19.48 | 4.56 | 32.54 |
| 19.96 | 4.45 | 25.28 |
| 20.48 | 4.34 | 12.00 |
| 20.82 | 4.27 | 19.68 |
| 21.09 | 4.21 | 16.95 |
| 22.04 | 4.03 | 100.00 |
| 22.31 | 3.99 | 23.46 |
| 23.28 | 3.82 | 29.94 |
| 23.56 | 3.78 | 28.32 |
| 24.13 | 3.69 | 9.79 |
| 24.55 | 3.63 | 3.98 |
| 25.25 | 3.53 | 59.45 |
| 25.62 | 3.48 | 21.16 |
| 26.78 | 3.33 | 2.90 |
| 27.22 | 3.28 | 1.78 |
| 28.03 | 3.18 | 3.50 |
| 29.40 | 3.04 | 2.58 |
| 30.75 | 2.91 | 5.46 |
| 31.22 | 2.86 | 4.08 |
| 33.92 | 2.64 | 3.15 |
| 35.23 | 2.55 | 5.58 |
| 36.13 | 2.49 | 1.53 |
| 36.59 | 2.46 | 1.07 |
| 37.69 | 2.39 | 3.43 |
| 38.31 | 2.35 | 1.78 |
| 39.56 | 2.28 | 1.29 |

Figure 2:
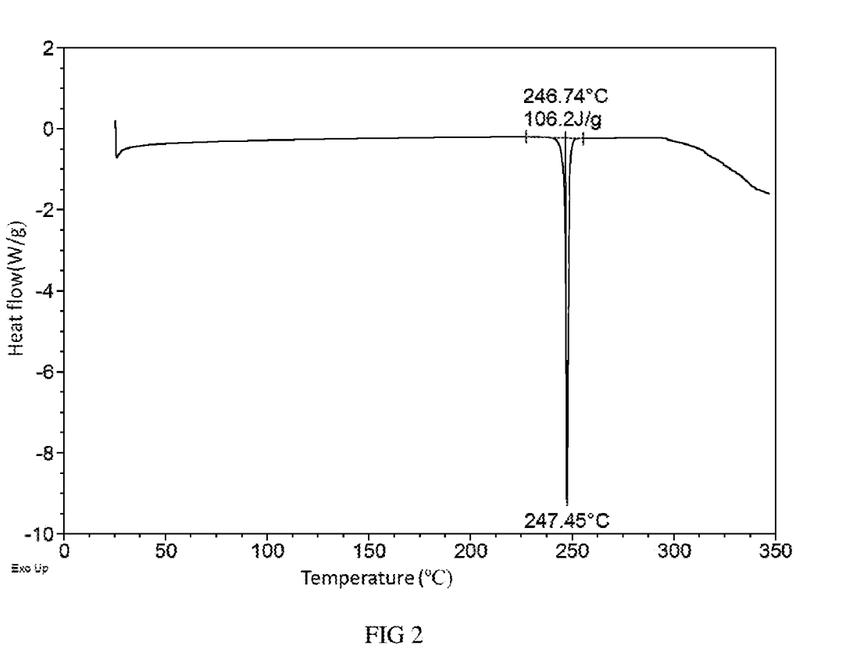
FIG. 2 shows a DSC curve of Form A in example 1.

When differential scanning calorimetry (DSC) was performed on Form A, an endothermic peak appeared with onset temperature at around 247° C., and the DSC curve is substantially as depicted in FIG. 2.

Figure 3:
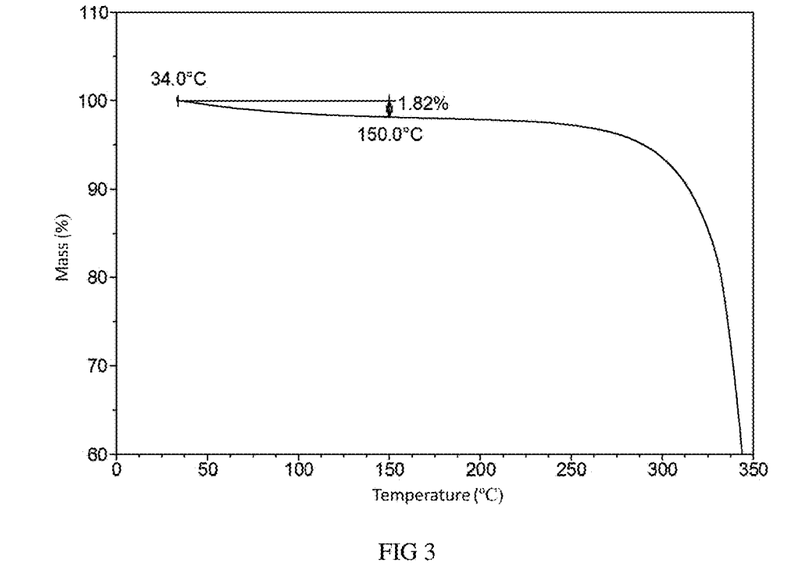
FIG. 3 shows a TGA curve of Form A in example 1.

When thermo gravimetric analysis (TGA) was performed on Form A, about 1.8% weight loss was observed when Form A was heated to 150° C., and the TGA curve is substantially as depicted in FIG. 3.

Figure 4:
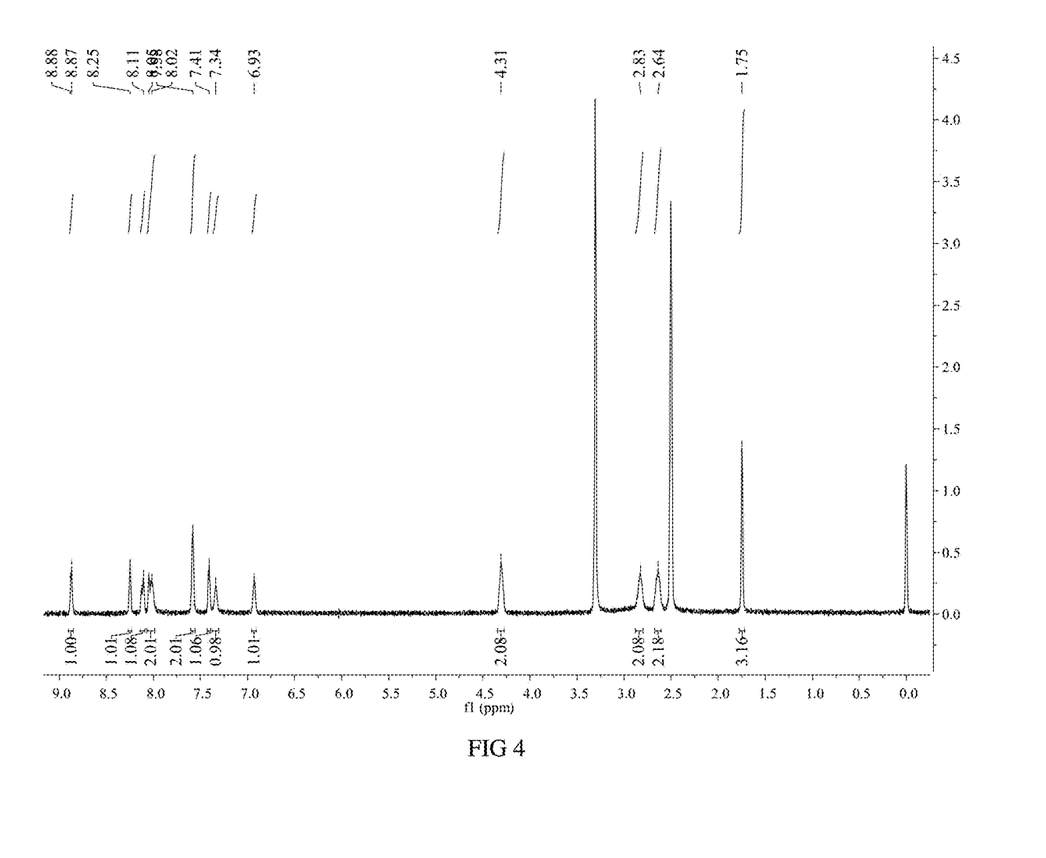
FIG. 4 shows a NMR spectrum of Form A in example 1.

The $^1$H NMR spectrum of Form A is substantially as depicted in FIG. 4, and the corresponding data are: $^1$H NMR (400 MHz, DMSO-d$^6$): δ 8.88 (d, J=4.2 Hz, 1H), 8.25 (s, 1H), 8.12 (d, J=7.2 Hz, 1H), 8.03 (d, J=11.9 Hz, 2H), 7.58 (d, J=3.7 Hz, 2H), 7.41 (d, J=3.4 Hz, 1H), 7.34 (s, 1H), 6.93 (s, 1H), 4.31 (s, 2H), 2.83 (s, 2H), 2.64 (s, 2H), 1.75 (s, 3H).

Example 2: Hygroscopicity of Form A

Dynamic vapor sorption (DVS) was applied to test hygroscopicity of Form A and Form 1 disclosed in WO2007018818A1 with about 10 mg of samples. The results are listed in Table 2.

TABLE 2

| | Relative humidity (RH) | | |
|---|---|---|---|
| Crystalline form | Weight gain at 80% RH | Weight gain at 95% RH | Solid Form after DVS test |
| Form 1 | 0.33% | 0.53% | Form 1 (slightly amorphous) |
| Form A | 0.15% | 0.23% | Form A (no change) |

Figure 5:
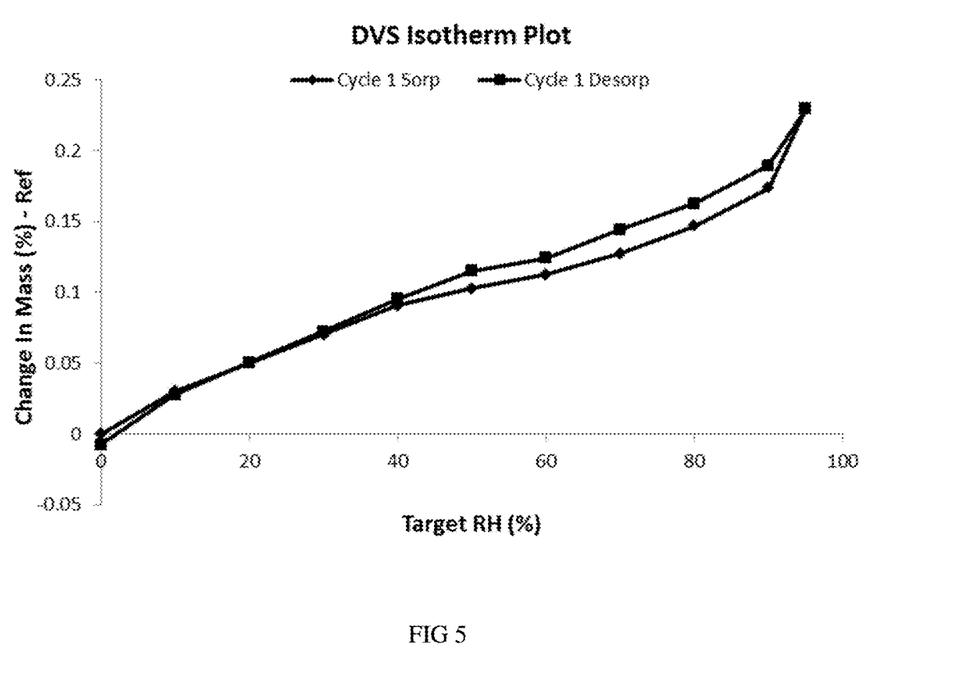
FIG. 5 shows a DVS plot of Form A in example 2.
Figure 6:
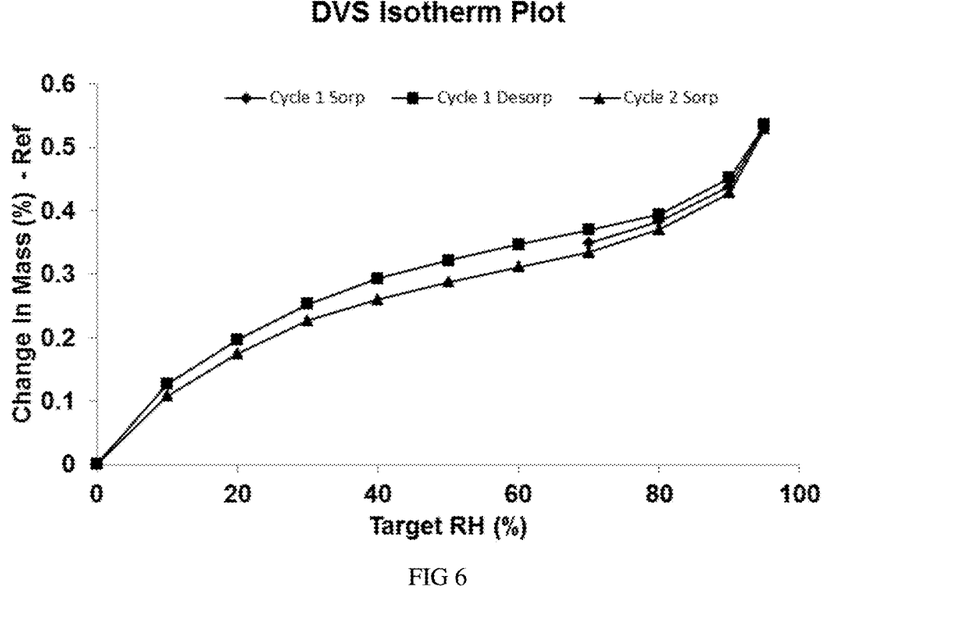
FIG. 6 shows a DVS plot of Form 1 in example 2.
Figure 7:
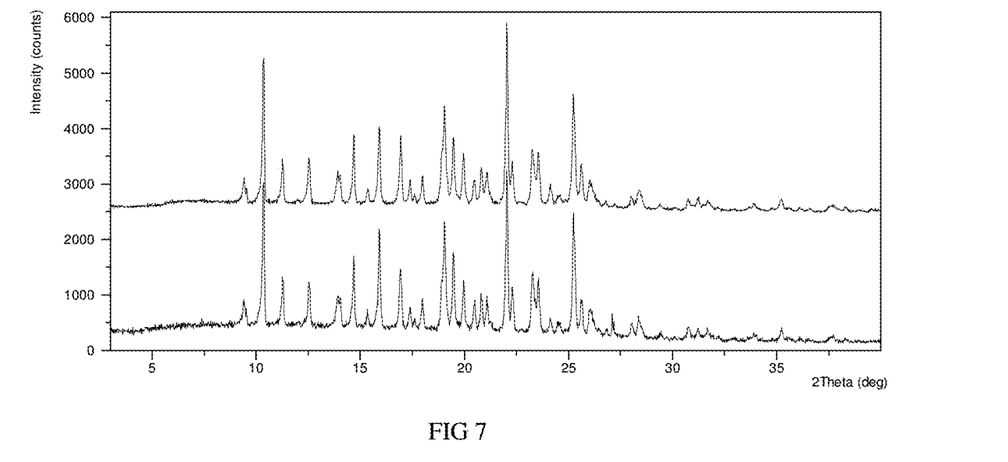
FIG. 7 shows the XRPD pattern overlay of Form A before and after DVS in example 2 (top: XRPD pattern before DVS test, bottom: XRPD pattern after DVS test).
Figure 8:
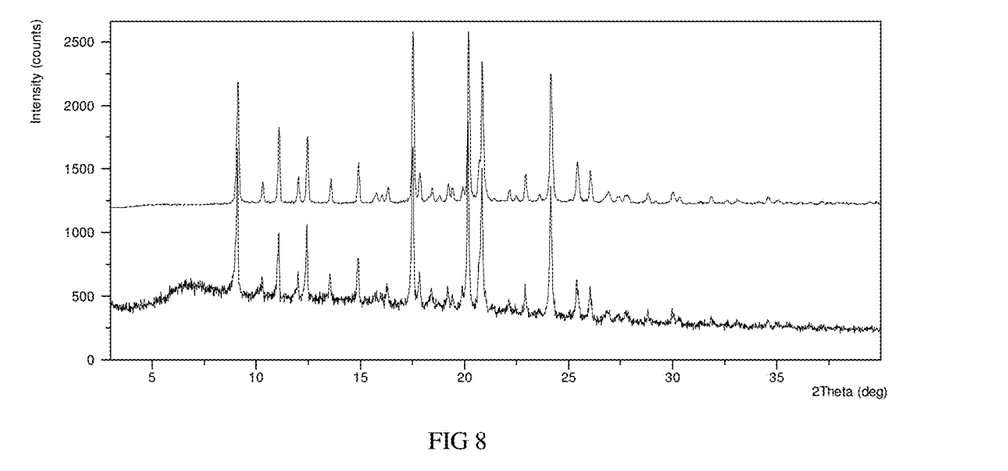
FIG. 8 shows the XRPD pattern overlay of Form 1 before and after DVS in example 2 (top: XRPD pattern before DVS test, bottom: XRPD pattern after DVS test).

The DVS plots of Form A and Form 1 are substantially as depicted in FIG. 5 and FIG. 6. The XRPD pattern overlay of Form A and Form 1 before and after DVS is substantially as depicted in FIG. 7 and FIG. 8 (top: XRPD pattern before DVS test, bottom: XRPD pattern after DVS test).

Description and definition of hygroscopicity (Chinese Pharmacopoeia 2015 edition, 9103 General drug hygroscopic test guidelines, test at 25° C.±1° C., 80% RH).

Deliquescent: Sufficient water is absorbed to form a liquid;

Very hygroscopic: Increase in mass is equal to or greater than 15 percent;

Hygroscopic: Increase in mass is less than 15 percent and equal to or greater than 2 percent;

Slightly hygroscopic: Increase in mass is less than 2 percent and equal to or greater than 0.2 percent.

Non-hygroscopic or almost non-hygroscopic: increase in mass is less than 0.2%.

Weight gain of Form A at 80% RH is 0.15%. Form A is non-hygroscopic or almost non-hygroscopic. Weight gain of Form 1 of the prior art at 80% RH is 0.33%. Form 1 is slightly hygroscopic. The hygroscopicity of Form A is superior to that of Form 1 of the prior art. Form A is not susceptible to high humidity to deliquescence.

The XRPD results show that the crystalline form of Form A of the present disclosure does not change after DVS test and keeps good crystallinity. After DVS test, Form A maintains stable physicochemical properties, which is suitable for drug preparation, storage and production process.

Example 3: Kinetic Solubility

Form A of the present disclosure and Form 1 of the prior art were suspended into FaSSIF (Fasted state simulated intestinal fluids, pH=6.5), FeSSIF (Fed state simulated intestinal fluids, pH=5.0), SGF (Simulated gastric fluids, pH=1.8) and water to get saturated solutions. After equilibrated for 1 h, 4 h and 24 h, concentrations of the saturated solutions were measured by HPLC. The results are listed in Table 3.

TABLE 3 results of kinetic solubility experiment

|  |  | FaSSIF | | FeSSIF | | H₂O | |
|---|---|---|---|---|---|---|---|
|  | time | Form 1 | Form A | Form 1 | Form A | Form 1 | Form A |
| solubility (mg/mL) | 1 h | 0.058 | 0.23 | 0.12 | 0.48 | 0.056 | 0.17 |
|  | 4 h | 0.051 | 0.27 | 0.11 | 0.82 | 0.055 | 0.25 |
|  | 24 h | 0.052 | 0.52 | 0.12 | 0.64 | 0.055 | 0.31 |

From the results of kinetic solubility in Table 53, the solubility of Form A of the present disclosure is significantly higher than that of the prior art Form 1 at each sampling point. The solubility of Form 1 is less than 0.06 mg/mL in both FaSSIF and H₂O. The solubility of Form A of the present disclosure is 3 to 10 times higher than that of Form 1 in FaSSIF and H₂O, and 4 to 8 times higher than that of Form 1 in FeSSIF, indicating that Form A has better solubility in FaSSIF, FeSSIF and water, and Form A has achieved unexpected effects.

Example 4: Particle Size Comparison Experiment

The results of particle size distribution are shown in table 4

TABLE 4 particle size distribution

| Solid form | Ultrasonication time (s) | MV (μm) | D10 (μm) | D50 (μm) | D90 (μm) |
|---|---|---|---|---|---|
| Form 1 | 0 | 62.25 | 33.41 | 56.97 | 95.11 |
|  | 30 | 45.75 | 24.89 | 42.56 | 68.40 |
|  | 60 | 40.41 | 22.40 | 37.88 | 59.87 |
|  | 90 | 37.83 | 20.94 | 35.58 | 55.95 |
| Form A | 0 | 190.8 | 50.28 | 170.3 | 356.4 |
|  | 30 | 116.1 | 34.37 | 106.2 | 210.5 |
|  | 60 | 104.1 | 29.37 | 92.81 | 192.2 |
|  | 90 | 91.94 | 26.40 | 83.69 | 167.2 |

The abbreviations used in the present disclosure are explained as follows:

MV: Average particle size calculated by volume

D10: particle size which accounts for 10% of the particle size distribution (volume distribution)

D50: particle size which accounts for 50% of the particle size distribution (volume distribution)

D90: particle size which accounts for 90% of the particle size distribution (volume distribution)

The results show that Form A of the present disclosure has a larger particle size. An increase in particle size in the production process is beneficial for product separation, filtration and purification.

Example 5: Mechanical Stability

Figure 9:
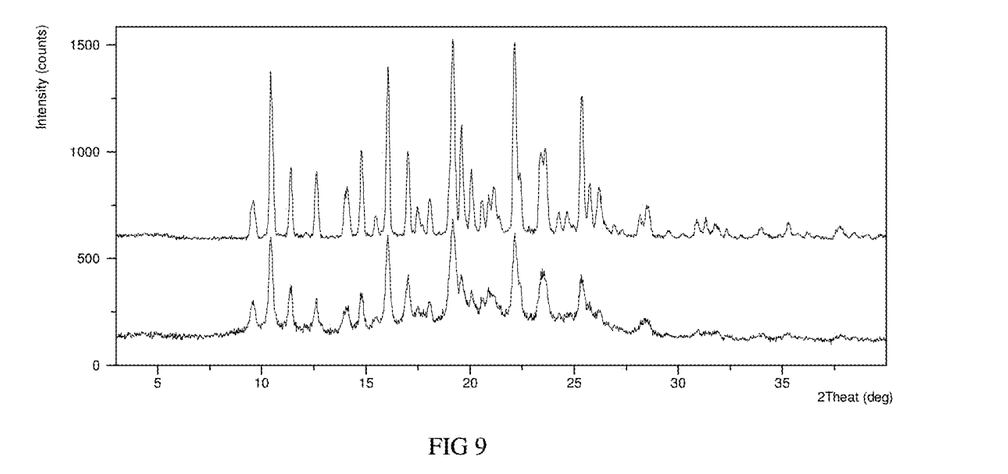
FIG. 9 shows the XRPD pattern overlay of Form A before and after grinding in example 5 (top: XRPD pattern before grinding, bottom: XRPD pattern after grinding).

Solid sample of Form A of the present disclosure was ground manually for 5 minutes in mortar. The XRPD pattern overlay of the solids before and after grinding is substantially as depicted in FIG. 9 (top: XRPD pattern before grinding, bottom: XRPD pattern after grinding). The XRPD pattern doesn't change significantly before and after grinding, indicating that Form A can maintain stable physicochemical properties under certain mechanical stress.

Example 6: Long-Term and Accelerated Stability

Solid samples of Form A and Form 1 were stored under different conditions of 25° C./60% RH, 40° C./75% RH. 60° C./75% RH and 80° C. The results are shown in Table 5

TABLE 5 stability experiment results

| Initial form | Conditions | Time | Solid form |
|---|---|---|---|
| Form 1 | 25° C./60% RH | 12 months | Form 1 |
|  | 40° C./75% RH | 12 months | Form 1 |
|  | 60° C./75% RH | 2 weeks | Form 1 |
|  | 80° C. | 2 weeks | Form 1 + Form A |
| Form A | 25° C./60% RH | 12 months | Form A |
|  | 40° C./75% RH | 12 months | Form A |
|  | 60° C./75% RH | 2 weeks | Form A |
|  | 80° C. | 2 weeks | Form A |

Figure 10:
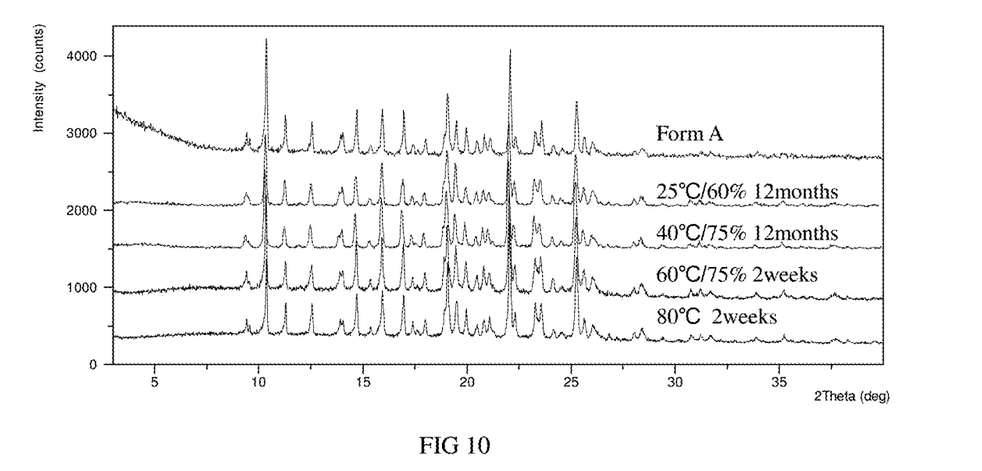
FIG. 10 shows the XRPD pattern overlay of Form A before and after stability test in example 6 (from top to bottom: the initial Form A and samples of Form A stored at 25° C./60% RH for 12 months, 40° C./75% RH for 12 months, 60° C./75% RH for 2 weeks, and 80° C. for 2 weeks.)
Figure 11:
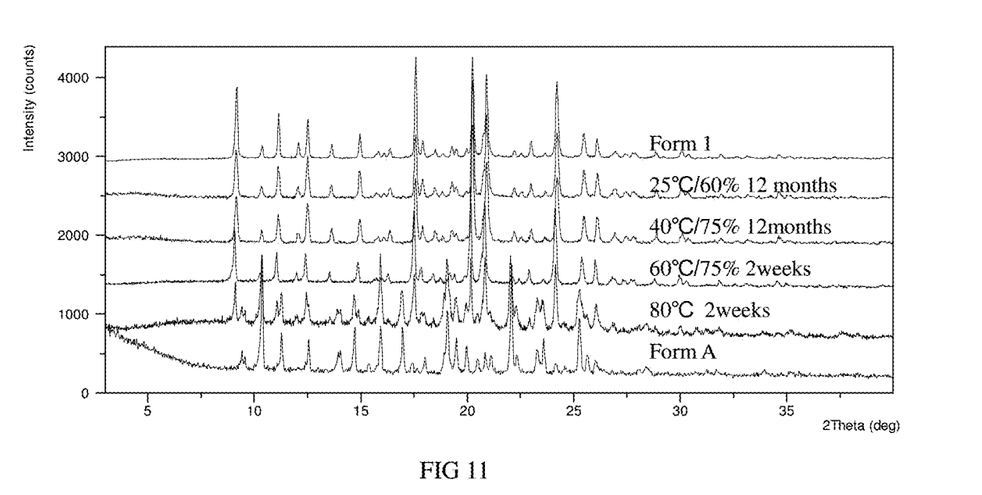
FIG. 11 shows the XRPD pattern overlay of Form 1 before and after stability test in example 6 (from top to bottom: the initial From 1 and Form 1 stored at 25° C./60% RH for 12 months, Form 1 stored at 40° C./75% RH for 12 months, Form 1 stored at 60° C./75% RH for 2 weeks, Form 1 stored at 80° C. for 2 weeks and the initial Form A.)

The results show that form A keeps stable for at least 12 months at 25° C./60% RH and 40° C./75% RH, at least 2 weeks at 60° C./75% RH and 80° C., indicating that Form A has good stability at room temperature/high temperature/ high humidity conditions. However, the stability of Form 1 at high temperature is poor. Form 1 partially converts to Form A after being stored at 80° C. for two weeks. The XRPD overlays of Form A and Form 1 under different conditions are substantially as depicted in FIG. 10 and FIG. 11, respectively.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure

What is claimed is:

1. A crystalline form A of Galunisertib, wherein the X-ray powder diffraction pattern shows characteristic peaks at 2theta values of 22.0°±0.2°, 10.4°±0.2° and 25.3°±0.2° using CuKα radiation.

2. The crystalline form A according to claim 1, wherein the X-ray powder diffraction pattern shows 1 or 2 or 3 characteristic peaks at 2theta values of 15.9°±0.2°, 14.7°±0.2° and 16.9°±0.2° using CuKα radiation.

3. The crystalline form A according to claim 1, wherein the X-ray powder diffraction pattern shows 1 or 2 or 3 characteristic peaks at 2theta values of 19.5°±0.2°, 12.5°±0.2° and 20.0°±0.2° using CuKα radiation.

4. The crystalline form A according to claim 2, wherein the X-ray powder diffraction pattern shows 1 or 2 or 3 characteristic peaks at 2theta values of 19.5°±0.2°, 12.5°±0.2° and 20.0°±0.2° using CuKα radiation.

* * * * *